United States Patent
Tsubouchi et al.

(10) Patent No.: US 6,440,740 B1
(45) Date of Patent: Aug. 27, 2002

(54) MATERIAL FOR ACTIVATING EPIDERMAL CELL MULTIPLICATION

(75) Inventors: Kozo Tsubouchi, 15-8, Matsumaedai 6-chome, Moriya-cho, Kitasouma-gun, Ibaraki, 302-0102; Hiromi Yamada, A107 Tokeidai-haitsu, 8-10, Ninomiya 1-chome, Tsukuba-shi, Ibaraki, 305-0051; Yoko Takasu, 504, 14-301, Namiki 2-chome, Tsukuba-shi, Ibaraki, 305-0044, all of (JP)

(73) Assignees: Japan as represented by Director General of National Institute of Sericultural and Entomological Science, Ministry of Agriculture, Forestry and Fisheries, Tsukuba; Kozo Tsubouchi, Kitasouma-gun; Hiromi Yamada; Yoko Takasu, both of Tsukuba, all of (JP)

( * ) Notice: Subject to any disclaimer, the term of this patent is extended or adjusted under 35 U.S.C. 154(b) by 0 days.

(21) Appl. No.: 09/341,973
(22) PCT Filed: Nov. 16, 1998
(86) PCT No.: PCT/JP98/05150
§ 371 (c)(1), (2), (4) Date: Jul. 16, 1999
(87) PCT Pub. No.: WO99/25811
PCT Pub. Date: May 27, 1999

(30) Foreign Application Priority Data

Nov. 18, 1997 (JP) .............................. 9-333560

(51) Int. Cl.$^7$ .................................................. C12N 5/00
(52) U.S. Cl. ........................ 435/402; 435/325; 435/405; 424/445; 424/447; 424/537
(58) Field of Search ................................ 435/325, 402, 435/405; 424/445, 447, 537

(56) References Cited

U.S. PATENT DOCUMENTS 4,233,212 A * 11/1980 Otoi et al.
4,820,418 A * 4/1989 Hirotsu et al.
5,385,836 A * 1/1995 Kimura et al.

* cited by examiner

Primary Examiner—Leon B. Lankford, Jr.
(74) Attorney, Agent, or Firm—Flynn, Thiel, Boutell & Tanis, P.C.

(57) ABSTRACT

The present invention provides a novel material for activating epidermal cell multiplication on which not only effective adhesion and multiplication of human and mammalian epidermal cells is accomplished also intercellular adhesion is promoted to form a plain cellular layer. The present invention provides a material for activating epidermal cell multiplication which contains silk fibroin of α-type or α-helix X-ray diffraction pattern as a principal constituent. The present material fulfills the principal requirements for activating epidermal cells of greatly improved cellular adhesion rate, multiplication, intercellular adhesion and growth of cell layers.

10 Claims, 8 Drawing Sheets

FIG. 1

X-ray diffraction image of α-type silk fibroin

FIG. 2

X-ray diffraction image of β-type silk fibroin

FIG. 3 keratinized human epidermal cells after 5-hour incubation            after 20-hour incubation

FIG. 4

FIG. 5 keratinized human epidermal cells

FIG. 6 bird's-eye view of human epidermal cells after 20-hour incubation

FIG. 7 bird's-eye view of human epidermal cells after 20-hour incubation

FIG. 8 bird's-eye view of human epidermal cells after 20-hour incubation

MATERIAL FOR ACTIVATING EPIDERMAL CELL MULTIPLICATION

TECHNICAL FIELD

The present invention relates to a material for activating adhesion, multiplication and cell-layer formation of epidermal cells of human and mammalian types.

The present active material is useful as an epidermal cell-culture bed and a defect skin repairing material or wound coating material for vital tissue.

BACKGROUND TECHNOLOGY

Cells are capable of obviously or latently self-multiplying as an essential unit of life, while each of organogenetic cells in multicellular organisms differentiates into various functional cells in a predetermined manner of multiplication.

In the case of the epidermis which protects an organism from the outside environment, cells are formed as a laminar layer to cover dermis situating under the epidermis and multiply only by adhering to other vital tissues or artificial materials to form a planar layer.

More specifically, the human epidermis comprises several layers and unevenly comes in contact with the dermis under the cellular layers through a basal layer so that the epidermis has a larger contact surface to maintain a close relationship with the dermis.

The epidermis has a so-called sebaceous membrane as a thin outermost lipid layer which functions to prevent water from evaporating, and under the membrane there are water-containing keratinous layers mainly consisting of keratin.

Each cell is arranged as a layer under the keratinous layer to form a cellular layer which comes in contact with a basal layer.

These cells repeatedly divide on the basal layer to develop new cells. That is, the basal layer is a base where new cells are formed and developed.

Epidermal cells thus formed in the basal layer gradually rise to the surface and then die when they arrive at the skin surface, thereby cell nuclei disappearing to form a keratinous layer.

As described above, the basal layer is located in the innermost part of the epidermis as a complicatedly uneven layer to form the contact surface so as to keep a close relationship with the epidermal cellular layer.

Although the formation and multiplication of epidermal cells on the basal layer was unsuccessful for reproduction in vitro for a long time, it has recently been possible to conduct the in vitro multiplication thereof because various kinds of solid surface base-beds for adhering epidermal cells were developed.

Even in such an in vitro multiplication, however, it has been quite difficult to form a plain cellular layer similar to that of in vivo multiplication for the lack of mutual adhesion of the cells.

Synthetic high polymer materials, such as polystyrene, natural high polymer materials such as collagen, and synthetic high polymer materials coated with natural materials have been conventionally developed as a cell culture bed. However, as these materials are not always the multiplication of epidermal cells, development of a novel cell culture bed has been desired.

Recently, there was proposed a cell culture bed comprising a water-insoluble silk membrane as a natural high polymer (see, JP-A No. 4-41,595).

The above mentioned cell culture bed is a β-type silk membrane prepared by crystallizing an amorphous silk membrane with an alcohol to water-insolubilize it, and which the animal cellular adhesion rate is improved compared with a conventional polystyrene culture bed.

As a matter of course, improved adherence to the bed is essentially necessary to epidermal cell cultures, while it is also required to form a plain cellular layer in which adjacent cells strongly adhere with each other.

Particularly, to apply such an epidermal cell culture technique to a wound healing method, it is still expected to develop a culture bed which promotes formation of a plain cellular layer.

Accordingly, it is an object of the present invention to provide a novel material for activating epidermal cell multiplication in which are effective adhesion and multiplication of human and mammalian epidermal cells to a base-bed surface obtained but also intercellular adhesion is promoted to form a plain cellular layer.

A further object of the present invention is to provide a novel culture bed in which in vitro formation of human and mammalian epidermal cellular layers can be conducted.

A still further object of the present invention is to provide a wound coating material for healing a skin defect region or wound of humans and mammals.

Another object of the present invention is to contribute to the basic study of epidermal functions by conducting the in vitro development of epidermal cells and also to the investigation of the action mechanism of skin defect healing by means of a novel material for activating epidermal cell multiplication.

DISCLOSURE OF THE INVENTION

The inventors have investigated in detail the interaction between crystal form of silk protein and epidermal cells and finally found that silk protein of a crystal form having a backbone helix structure, and especially α-type or α-helix silk fibroin is an outstanding material for achieving the above mentioned objects.

The present invention is based on this information and provides a material for activating epidermal cell multiplication, an epidermal cell culture bed in which the present material is used as a culture bed for cell multiplication, and a wound coating material in which the present material is used on the wound.

According to the present invention, there is provided (1) a material for activating epidermal cell multiplication which comprises silk fibroin of the α-type or having an α-helix X-ray diffraction pattern as a principal constituent.

There is also provided (2) a material for activating epidermal cell multiplication which comprises silk fibroin of α-type or having an α-helix X-ray diffraction pattern as a principal constituent and 50% by weight or less of a synthetic polyamino acid of an α-helix crystalline form.

There is also provided (3) a material for activating epidermal cell multiplication described in item (1) or (2) in which said material is in the form of a fiber, membrane or powder.

There is also provided (4) a material for activating epidermal cell multiplication in which a solid surface of organic or inorganic substances is coated with a coating containing silk fibroin of α-type or having an α-helix X-ray diffraction pattern as a principal constituent.

There is also provided (5) an epidermal cell culture bed which comprises a coating containing silk fibroin of α-type or having an α-helix X-ray diffraction pattern as a principal constituent.

There is also provided (6) an epidermal cell culture bed in which a solid surface of organic or inorganic substances is coated with a stuff containing silk fibroin of α-type or α-helix X-ray diffraction pattern as a principal constituent.

There is also provided (7) an epidermal cell culture bed described in item (5) or (6) in which said bed is in the form of a membrane.

There is provided (8) a wound coating material which comprises a silk fibroin of α-type or having α-helix X-ray diffraction pattern as a principal constituent.

There is also provided (9) a wound coating material which comprises silk fibroin of α-type or having an α-helix X-ray diffraction pattern as a principal constituent and 50% by weight or less of a synthetic polyamino acid of α-helix crystalline form.

There is also provided (10) a wound coating material described in item (8) or (9) in which said material is in the form of a fiber, membrane or powder.

There is also provided (11) a wound coating material in which a solid surface of organic or inorganic substances is coated with a coating containing silk fibroin of α-type or having an α-helix X-ray diffraction pattern as a principal constituent.

A material for activating epidermal cell multiplication of the present invention is a material in which human and mammalian epidermal cells effectively adhere to a basal surface and multiply while forming a plain layer as a result of intercellular adhesion, i.e., a material in which adhesion and multiplication of epidermal cells as well as formation of a multicellular layer can be promoted.

A concept of the present invention also includes an epidermal cell culturing bed and a wound coating material.

Further, the present material is not limited to a specific shape or structure and may be in the form of a membrane such as sheet or film, powder, bead, fiber, etc.

All of the following may be used as raw materials for preparing a material for activating epidermal cell multiplication of the present invention:

a) Raw materials selected from cocoon yarn, raw silk yarn, silk fabric, silk yarn (fibroin fiber) or untreated products thereof;

b) Fibroin or sericin independently separated and prepared from cocoon yarn, raw silk yarn, silk fabric, silk yarn or untreated products thereof;

c) Raw materials prepared by mixing a material selected from cocoon yarn, raw silk yarn, silk fabric, silk yarn or untreated products thereof and independently separated and prepared fibroin or serine; and d) Protein fibrous materials produced by silkworms including domestic and wild-silkworms, such as, for example, used products of sericin- or fibroin-containing fiber, powder, film, etc., and liquid silk contained in a silk worm.

The amount of sericin contained in these raw materials is preferably 40% or less, and more preferably 20% or less from the standpoint of phase separation.

Further, not more than 50% by weight of a synthetic polyamino acid having a helical structure may be mixed with the above mentioned raw materials from the standpoint of formability. Such a polyamino acid includes those materials which have a backbone repeating unit of —A—, —A—G—, —A—G—S—, —A—G—A—G—S—, etc., wherein A, G and S represent alanine, glycine and serine, respectively. When independently prepared fibroin is used as a raw material, for example, the above mentioned synthetic polyamino acid having a helical structure may be mixed thereto in an amount of not more than 50% by weight.

A raw material used in the present invention, containing silk fibroin as a principal constituent, is a material in which silk fibroin is converted to α-type or has an α-helix structure by an α-crystallizing process as will be described in the following.

α-crystallization

Fibroin- and sericin-containing raw materials are degummed, dissolved in an aqueous solvent in the presence of a neutral salt and desalted to yield an aqueous fibroin solution, which is then cast on a smooth solid surface and dried to form a water soluble dry silk membrane.

Then, in order to convert the thus formed membrane to be water insoluble and in the form of a sheet or film having a crystal form of α-type or an α-helix structure, environmental moisture (for example, relative humidity of about 80 to 90%) is controlled to maintain a water content within 40±15% at room temperature and left to stand for such a long period of time as 12 to 24 hours. More specifically, the above mentioned process is conducted as in the following.

1) Crystallization in the course of drying

The aqueous fibroin solution is cast on a smooth solid surface and then dried to a water content of 40±15% in a drying step, which is kept for a long period of time under this condition.

2) Crystallization after drying

The aqueous fibroin solution is dried and kept as it is at room temperature and a water content of 40±15% for a long period of time.

The thus prepared water insoluble silk membrane of α-type or having an α-helix structure is dried and powdered to form a powdery material.

The thickness of the silk membrane is an important factor. If the silk membrane is comparatively thin, the molecular structure thereof is affected by a substrate material and does not always results in satisfied crystalline form. If the membrane is rather thick, on the other hand, it is apt to release from the substrate material.

From the above mentioned viewpoint, the silk membrane is preferably 0.05 to 20 μm, and more preferably 0.5 to 10 μm in thickness.

According to the present invention, it is possible to provide a greatly improved material which has greatly improved properties as essential requirements for activating epidermal cells, such as cell adhesion, multiplicity, intercellular adhesion, stretchability of cellular layer, etc.

It is therefore expected that the present invention can considerably contribute to the solution of the main problems in epidermal studies, for example, a biochemical reaction occurring when an epidermal cellular layer is formed, or to application of epidermal cell culture technology for care of wound skin.

BEST MODE FOR CARRYING OUT THE INVENTION

The present invention will be described in detail in the following embodiments, however, it is to be understood that the present invention is not restricted to these embodiments.

EXAMPLE 1

Raw silk from a domestic silkworm was boiled in a 0.1%—$Na_2CO_3$ aqueous solution in a bath ratio of 100 times for two hours and dried to obtain degummed silk.

The thus degummed, sericin-free silk yarn having a fibroin content of 97% or more was dissolved in a calcium-ethanol-water solution in molar ratio of 1:2:8, respectively, and desalted through water dialysis to prepare an aqueous solution of silk fibroin.

This aqueous solution was poured in a cell culture flask of 35 mm in diameter (plastic flat bottom type) and dried at room temperature to form a film-like silk fibroin membrane on the bottom.

The silk membrane on the bottom of the culture flask was left to stand at room temperature in an environment of a relative humidity of about 90% to control the water content thereof to about 40%, which was further left as it is for 20 hours to promote α-conversion.

Figure 1:
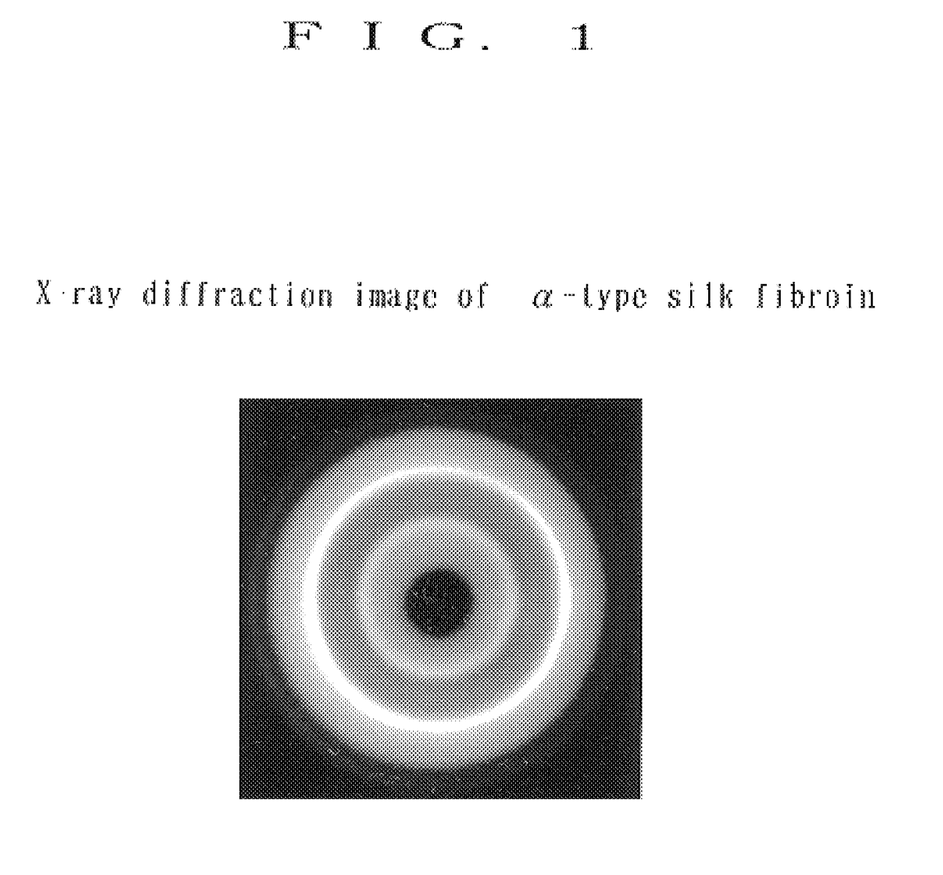
FIG. 1 is an X-ray diffraction image of an α-type silk fibroin prepared by Example 1 of the present invention.

The thus formed α-type fibroin membrane was partially peeled off to use for X-ray diffraction. The results of X-ray diffraction is shown in FIG. 1.

It is confirmed by X-ray diffraction that a silk fibroin membrane having an α-type crystalline structure is obtained. Determination of such α-type structure is detailed in "Kobunshi Ronbunshu" pp.453 to 462, Vol. 33, No. 8 (1976).

To the α-type silk fibroin membrane formed in the culture flask, a suspension of human epidermal cells of about 50,000 cells in 1 ml of culture liquid (culture medium K110 for epidermal cells available from Kyokuto Seiyaku Kogyo Co., Ltd.) was added and subjected to static culturing at a temperature of 37° C. in an incubator using a steam-saturated mixture of 5% of carbon dioxide gas and 95% of air.

Figure 3:
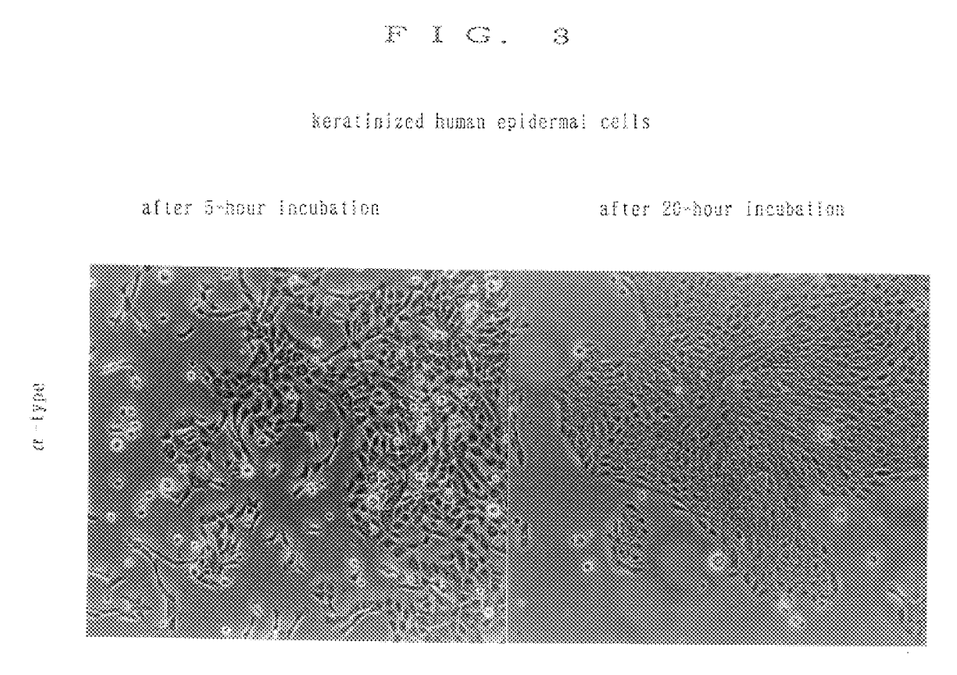
FIG. 3 is a phase contrast microscopic photograph of cells cultured in Example 1 of the present invention.

Phase contrast photomicrographs (100 magnifications) of cells after 5- and 20-hour incubations are shown in FIG. 3.

After 20-hour incubation, grown epidermal cells which adhered to the flask were separated by removing the culture liquid and washing out floating and dead cells therefrom with an isotonic sodium chloride solution, followed by addition of a trypsin solution at a temperature of 37° C.

The adhered extent or adhesion rate of the epidermal cells (%) was determined by microscopically counting the number of adhered cells.

The result is shown in Table 1.

TABLE 1

| material of cell culture bed | epidermal cell |
|---|---|
| silk film (α-type) | 98% |
| silk film (β-type) | 86% |
| no treatment (polystyrene) | 71% |

The adhesion rate of epidermal cells (%) is calculated by the following:

adhesion rate (%)=numbers of adhered cells after 20 hours/numbers of cells initially introduced to the flask ×100

Further, an additional static culture experiment was carried out in a similar manner as described above using the α-type silk fibroin membrane mixed with 35% by weight of a synthetic polyamino acid having an α-helix crystal form.

The additional experiment showed a similar result obtained by the α-type silk film shown in FIG. 3 and Table 1.

EXAMPLE 2

A wound coating material of a β-type silk fibroin crystalline powder was additionally prepared in this example as a reference to compare with that of the α-type.

α- and , β-type crystalline powders of silk fibroin were prepared as will be described below.

An aqueous solution of silk fibroin prepared in a similar manner as described in Example 1 was cast on an acrylic board and air-dried to form an amorphous membrane of about 30 μm in thickness.

Crystallization to α- and β-types was conducted as in the following.

The amorphous membrane was left to stand for one day in a room at a relative humidity of about 90% to control the moisture content thereof to about 40% so as to conduct α-crystallization.

On the other hand, β-crystallization was conducted by spraying a 70%—aqueous ethanol solution on the fibroin membrane.

These α- and β-type fibroin membranes were dried and physically ground to form powders having an average particle diameter of 50 βm or less.

The thus prepared α- and β-type crystalline powders were used as a wound coating material for a hairless dog to observe a healing effect thereof.

A back of the hairless dog were partially cut to dermis and peeled off to form three portions of 1 $cm^2$ each to be tested, which were then subjected to disinfection by dropping several drops of 0.05% glyconic add chorhexdine solution.

One of the wound portions was coated with the α-type crystalline powder, while the second portion was treated with the β-type. The third portion was left to stand as a control without any treatment. Each of three wound portions was protected by means of a permeable protector film (trade name of Tegadarm).

The result of skin tissue regeneration on the wound portions after one week is shown in Table 2.

TABLE 2

| days after wound | visual observation | wound coating material | | |
|---|---|---|---|---|
| | | α-type | β-type | control |
| 7 days | degree of inflammation | – | – | + |
| | epidermal regeneration | + | + | – |

(symbols – and +mean "less considerable" and "considerable", respectively)

It is apparent from Table 2 that the healing effect of the α- or β- type crystalline powder is higher than that of the control.

On the other hand, although the difference in the healing effect between the α- and β-types is not distinguishable by visual observation, it is confirmed by a more minute observation of tissue images that the α- type crystalline powder is more effective than the β-type.

Comparative Example 1 (β-crystallization)

Figure 2:
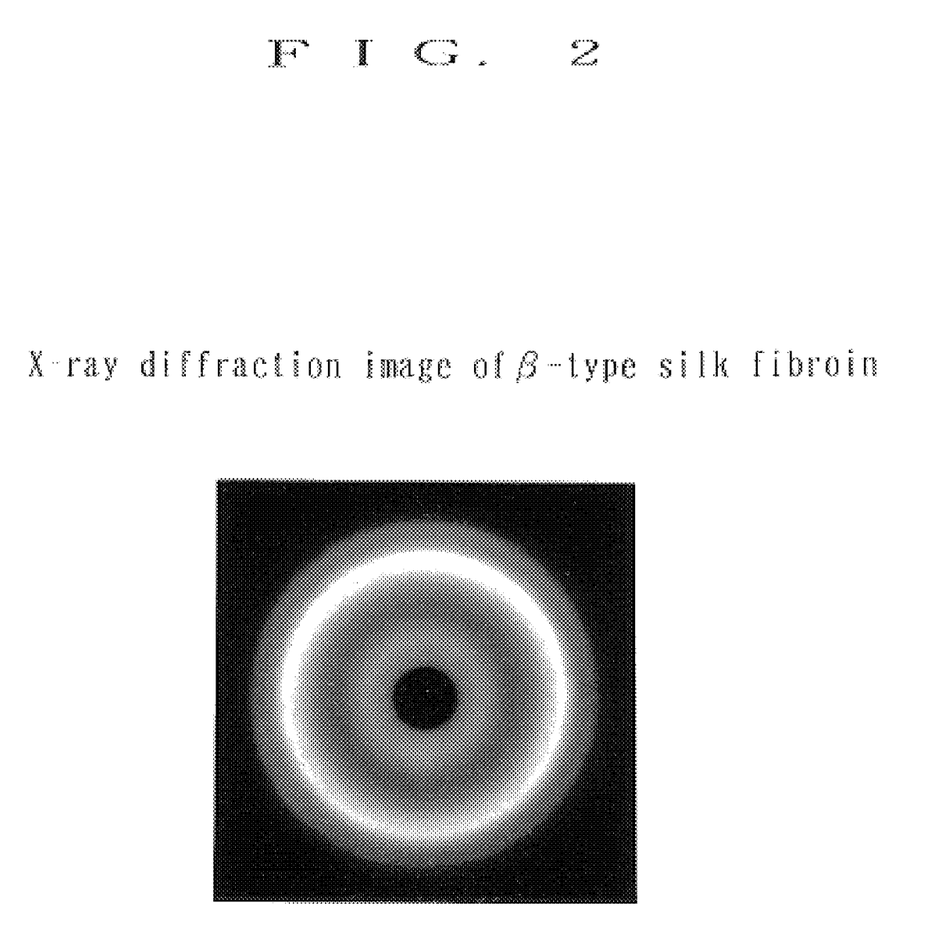
FIG. 2 is an X-ray diffraction image of a β-type silk fibroin prepared by Example 1 of the present invention.

Example 1 was repeated to form a crystallized silk fibroin membrane α- of βcrystallization in which a silk fibroin membrane before α-crystallization was dried on the bottom of a flask, subjected to a spray of a 70%—aqueous ethanol solution and further dried at room temperature. A X-ray diffraction image of the thus formed μ-type fibroin is shown in FIG. 2.

Figure 4:
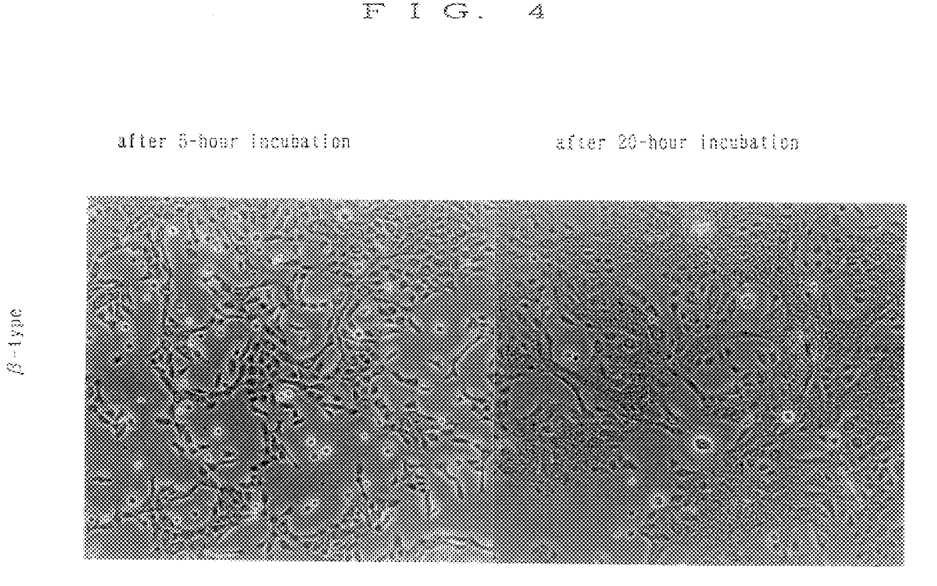
FIG. 4 is a phase contrast microscopic photograph of cells cultured in Comparative Example 1 of the present invention.

Phase contrast photomicrographs (100 magnifications) of cells after 5- and 20-hour incubations are shown in FIG. 4.

The adhesion rate (%) of epidermal cells after a 20-hour incubation was obtained in a similar manner as described in Example 1, which is shown in Table 1.

Comparative Example 2 (Polystyrene)

Human epidermal cells were subjected to static culturing similarly as described in Example 1 using a polystyrene flask ("FALCON 1008") commercially available from Becton Dickinson and Company.

Figure 5:
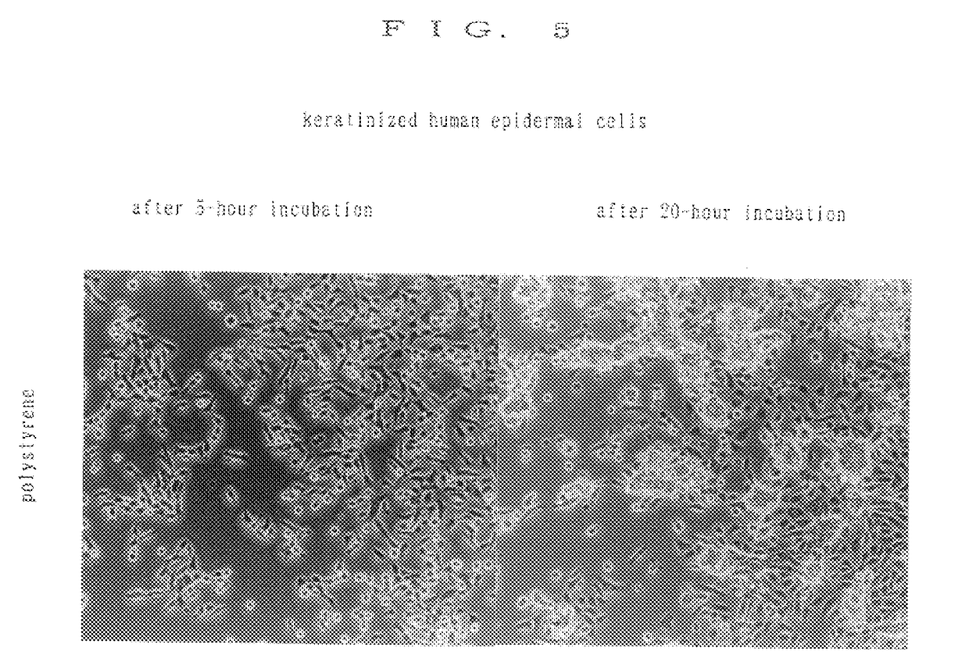
FIG. 5 is a phase contrast microscopic photograph of cells cultured in Comparative Example 2 of the present invention.

Phase contrast photomicrographs (100 magnifications) of cells after 5- and 20-hour incubations are shown in FIG. 5.

The adhesion rate (%) of the epidermal cells after a 20-hour incubation was obtained in a similar manner as described in Example 1, which is also shown in Table 1.

Figure 6:
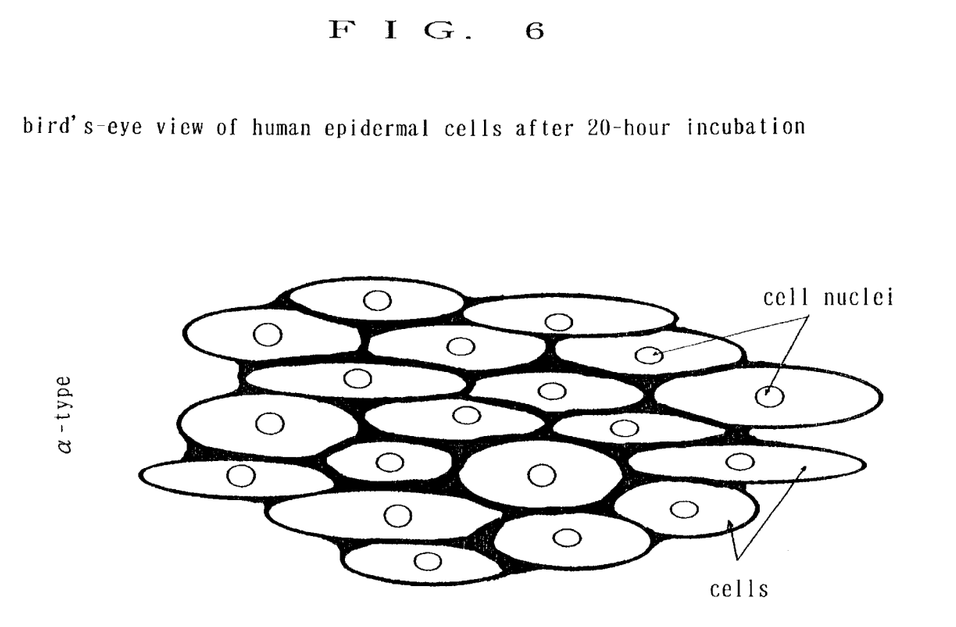
FIG. 6 is an illustration of cells cultured in Example 1 of the present invention.
Figure 7:
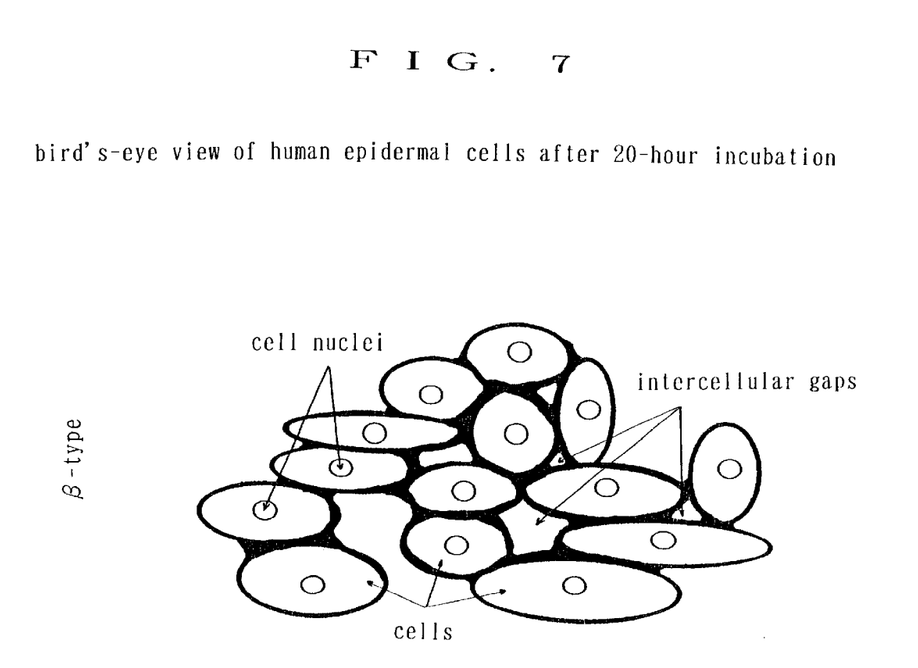
FIG. 7 is an illustration of cells cultured in Comparative Example 1 of the present invention.
Figure 8:
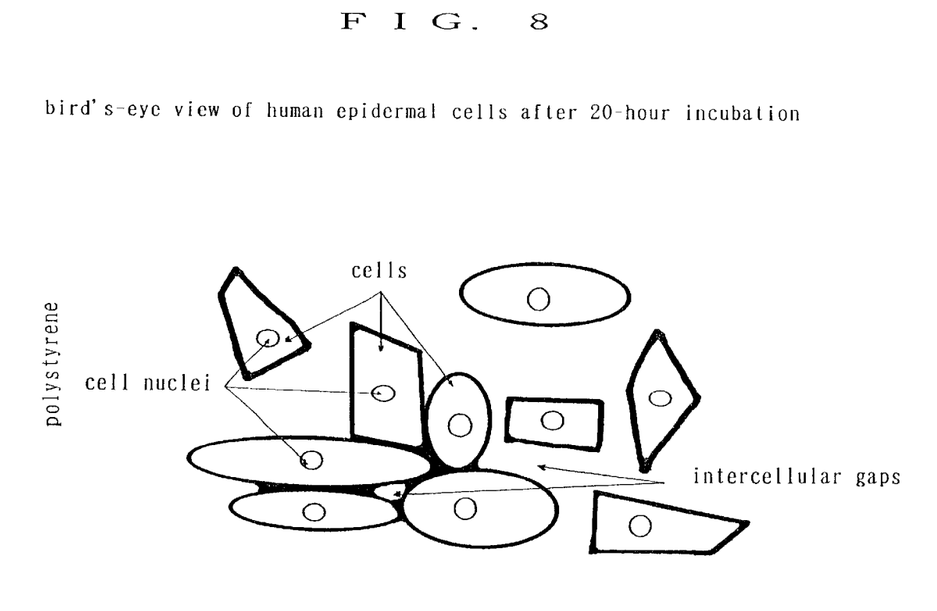
FIG. 8 is an illustration of cells cultured in Comparative Example 2 of the present invention.

When a material for activating epidermal cell multiplication of the present invention is used as a culture bed for culturing human epidermal cells, it is apparent that the cellular adhesion and multiplication thereof on the bed surface are conducted more homogeneously and, at the same time, the intercellular adhesion and growth of cell layers are greatly improved compared with Comparative Examples 1 and 2, as shown in FIGS. 6 to 8 (α-, β-types and polystyrene, respectively), which are bird's-eye views of FIGS. 3 to 5, and Table 1.

The reason is that the present material provides a fine and uneven surface like a basal layer membrane (basal membrane) of vital epidermis because of the helical structure thereof, yields close distribution of cells on the surface and promotes homogeneous adhesion and multiplication, thereby forming a cellular layer similar to that of vital epidermis.

Further, intercellular gaps are seldom observed in FIG. 6 (α-type) and are considerable in FIG. 7 (β-type), while in FIG. 8 (polystyrene), the intercellular contact itself is rather few and the contour of cells is heterogeneous.

Industrial Applicability

The present material, which promotes adhesion, multiplication and cellular layer formation of human and mammalian epidermal cells, is not only useful as a culture bed for epidermal cells and a wound coating material, but may be potentially used for other purposes of studying biochemical reactions during cellular layer formation of epidermal cells, or applying to wound skin care, stock breeding, etc.

What is claimed is:

1. A material for activating epidermal cell multiplication in which the improvement comprises said material containing silk fibroin of the α-type or having an α-helix X-ray diffraction pattern and 50% by weight or less of a synthetic polyamino acid of an α-helix crystalline form.

2. A material for activating epidermal cell multiplication as claimed in claim 1, wherein said material is in the form of a membrane, powder, bead or fiber.

3. A material for activating epidermal cell multiplication as claimed in claim 1, wherein said synthetic polyamino acid comprises alanine.

4. A material for activating epidermal cell multiplication as claimed in claim 3, wherein said synthetic polyamino acid additionally comprises glycine.

5. A material for activating epidermal cell multiplication as claimed in claim 4, wherein said synthetic polyamino acid additionally comprises serine.

6. A wound coating material in which the improvement comprises said material containing silk fibroin of the α-type or having an α-helix X-ray diffraction pattern and 50% by weight or less of a synthetic polyamino acid of α-helix crystalline form.

7. A wound coating material as claimed in claim 6, wherein said material is in the form of a membrane, powder, bead or fiber.

8. A wound coating material as claimed in claim 6, wherein said synthetic polyamino acid comprises alanine.

9. A wound coating material as claimed in claim 8, wherein said synthetic polyamino acid additionally comprises glycine.

10. A wound coating material as claimed in claim 9, wherein said synthetic polyamino acid additionally comprises serine.

* * * * *